United States Patent [19]

Weisman

[11] Patent Number: 5,141,755
[45] Date of Patent: Aug. 25, 1992

[54] REDUCED ANIMAL PRODUCT PET FOOD COMPOSITION

[76] Inventor: Eric H. Weisman, 815 S. Robert St., St. Paul, Minn. 55107

[21] Appl. No.: 706,647

[22] Filed: May 29, 1991

[51] Int. Cl.$^5$ .............................................. A23K 1/00
[52] U.S. Cl. ...................... 426/42; 426/72; 426/74; 426/454; 426/601; 426/623; 426/630; 426/634; 426/805
[58] Field of Search ................. 426/74, 72, 42, 2, 623, 426/630, 636, 805, 804, 601, 454, 634

[56] References Cited

U.S. PATENT DOCUMENTS

| | | | |
|---|---|---|---|
| 4,015,026 | 3/1977 | Burkwall et al. | 426/614 |
| 4,251,556 | 2/1981 | Burkwall et al. | 426/805 |
| 4,310,558 | 1/1982 | Nahm | 426/805 |
| 4,348,418 | 9/1982 | Smith et al. | 426/805 |
| 4,371,556 | 2/1983 | Pitchon et al. | 426/805 |
| 4,735,808 | 4/1988 | Scaglione et al. | 426/805 |
| 4,892,748 | 1/1990 | Andersen et al. | 426/72 |

*Primary Examiner*—R. B. Penland
*Attorney, Agent, or Firm*—Joel D. Skinner

[57] ABSTRACT

A reduced animal product pet food or non-animal pet food composition having a mixture of proteinaceous and farinaceous components in an amount sufficient to provide a nutritionally balanced, dry pellet. The pet food composition includes a non-meat based animal fat substance and a vegetable based fat substance. The non-meat based animal fat substance is preferably an egg or dairy based fat substance. Lactase, pectin, hyperfortified vitamin, and flavoring components are also provided.

12 Claims, No Drawings

REDUCED ANIMAL PRODUCT PET FOOD COMPOSITION

BACKGROUND OF THE INVENTION

This invention relates generally to an animal food formulation, and more particularly, to pet food formulations such as dog foods and cat foods.

Prior art pet foods typically use large quantities of fat from slaughtered or rendered animals to enhance flavor, and to make it more palatable to pets and more attractive to pet owners. Animal fats, particularly meat based fats are further advantageous because they provide essential nutrients, for example amino acids, which are not present in other common feed components. However, the use of meat based fats and animal by-products in prior art pet foods pose significant problems. High amounts of animal products in prior art pet foods, particularly meat based products such as fats, contribute to heart and other vascular diseases in pets. The use of high amounts of fats and other animal by-products also contribute to brutality at the slaughterhouse level.

In addition to the use of animal fats, prior art pet food formulations often contain animal by-products such as crushed bird feathers, animal digest, dried blood, intestinal content, and various other high nitrogen content materials. Rendered animals such as farm animals that die from disease or those killed at dog-cat pounds, animal labs, and road kill, and that are typically used in pet food often have high amounts of cadmium and mercury in their flesh. Hydrochloric acid is often used to digest either animal parts or the whole animal and the residue is put in pet food. Such materials are typically high in free radical content which has been linked to increased cell aging and cancer, as well as heart, vascular, liver, kidney and other degenerative diseases.

As a result of these problems, it is desirable to provide a substitute for meat-based animal fats and by-products. However, such substitutes are somewhat limited in availability as well as effectiveness. One meat based fat substitute, heretofore unused in the animal feed industry as a source of essential nutrients, is dairy based fat. An apparent reason for the lack of use of such fats as a substitute is that dairy products, particularly lactose, are relatively indigestible by members of the canine family (Canidae). This lactose intolerance problem exists despite the high quality protein and fat content provided by dairy products such as butter fat, butter, cheese, and cheese by-products.

Another problem in prior art pet foods is that they do not contain sufficient levels of essential and desirable nutrients. Although such formulations typically contain vitamin supplements, they often do not contain necessary quantities of such vitamins. For example, during the process of preparing many pet food formulations, which frequently involves pressurizing, heating and steaming, vitamins and other nutrients are destroyed. As a result, initial vitamin levels are substantially reduced. Also, such vitamin supplements deteriorate during the shelf life of the pet food formulation. Still other pet food formulations do not provide sufficient vitamin quantities such that animals with impaired or decreased intestinal absorption can derive necessary nutrients at low vitamin concentrations.

Despite the need for a pet food formulation which provides high vitamin levels, low free radical levels, low cholesterol, low fat, and which overcomes the limitations of the prior art, none insofar is known has been proposed or developed.

Accordingly, it is an object of the present invention to provide a pet food composition which utilizes reduced amounts of animal products, particularly killed or rendered meat based animal products. Another object of this invention is to provide a pet food composition which is high in grain, legume, vegetable and fruit based constituents. A further object of this invention is to provide such a composition which is also high in nutrient value. And, it is an object of this invention to provide a composition having the aforementioned qualities, and further being highly palatable to pets.

SUMMARY OF THE INVENTION

The present invention provides a reduced animal product pet food composition, which comprises a mixture of proteinaceous and farinaceous components in an amount sufficient to provide a nutritionally balanced dry pellet, a non-meat based animal fat substance, and a vegetable based fat substance.

The proteinaceous components may include meal made from soybean or other high protein grains or vegetables. Farinaceous components preferably include ground corn, oats, rice, barley, and/or wheat flour. The mixture of these components is preferably provided in an amount of 10 to 30 percent by weight.

The non-meat based animal fat substance is preferably a dairy based fat substance, such as butter or cheese, but may alternatively be egg or an egg by-product. When a dairy based fat substance is used, the pet food composition further includes a metabolically effective amount of lactase. Lactase is provided in an amount of 0.001 to 10 percent by weight and preferably between 1 to 3 percent by weight. The non-meat based fat substance is preferably provided in an amount of approximately 4 to 35 percent by weight and preferably between 8 to 22 percent by weight.

In the most preferred embodiment, the pet food composition further comprises a hyperfortified vitamin mixture component, for example, provided in an amount of not less than 1.75 percent by weight and preferably between 1.75 to 8 percent by weight. This vitamin mixture is over 300 percent of the National Research Council requirements. Further, the pet food composition preferably includes a high concentration of pectin. Pectin is a complex carbohydrate that assists in removing fatty plaques from the inside walls of arteries.

These and other benefits of this invention will become clear from the following description.

DESCRIPTION OF THE PREFERRED EMBODIMENT

The Pet Food Formulation of this invention is a fortified, high protein pet food useable particularly for dogs and cats. Animals such as dogs and cats require a basic diet including carbohydrates, protein, fat, minerals and vitamins. Carbohydrates primarily supply energy (calories) for growth and activity. Protein primarily serves as a source of essential amino acids for growth and repair of tissues. Fat has a high nutritive value due to its high energy level and digestibility. Fat also contains essential fatty acids. Finally, minerals and vitamins are essential, as in humans, for proper cell function.

The composition of the present invention comprises a mixture of proteinaceous and farinaceous components in an amount sufficient to provide a nutritionally balanced, dry pellet, a non-meat based animal fat substance, and a vegetable based fat substance.

The proteinaceous components may include soybean or other legume or vegetable meal, corn or rice gluten meal, and wheat middlings (the fine, floury outer covering of wheat grain). Farinaceous components preferably include ground corn, oats, rice, barley, and/or wheat flour. This mixture is provided in an amount between 10 to 30 percent by weight.

Cereal grains provide carbohydrates high in biological energy value. Cereals also provide protein which is used primarily as a source of essential amino acids, and also for caloric intake. With the exception of soybean, cereal sources typically do not provide sufficient essential amino acids. Therefore, some animal based products are necessary to provide those essential amino acids lacking in cereal proteins. However, high fat diets are associated with a high incidence of atherosclerosis. High fat diets obtained from animal fats and flesh also have been associated with various forms of contamination, including heavy metal poisoning. Alternatively, high carbohydrate diets have been associated with obesity. Both such problems are avoided in the diet provided by this invention.

Animal fats are composed primarily of triglycerides, glycerol and fatty acids, primarily arachidonic, an essential unsaturated fatty acid. This fatty acid is necessary for metabolic reactions and in the production of cell membranes. Additionally, some intake of absorbable fat is necessary for the absorption of fat soluble vitamins.

The composition of the present invention does not utilize meat based animal fat. Required fats are instead provided by non-meat based animal fats, for example from dairy products such as butter or cheese. Alternatively, the non-meat based animal fat ingredient may comprise powdered whole egg. Egg also has complete groupings of fatty acids and is source of high amounts of protein. Thus, the formulations have reduced animal fat content and provide an ovo or lacto-ovo vegetarian pet diet. Non-meat based fat substance is provided in an amount of approximately 4 to 35 percent by weight, and preferably in a range of 8-22 percent by weight.

The non-meat based animal fat substance is preferably a dairy based fat substance, such as butter, cheese, or whey. Milk fat is the most complex of the natural fats, and of high nutritional value. Milk fat contains approximately 140 different fatty acids, depending upon the cow's diet. Milk protein present in dairy substances is also of high nutritional value in that it contains high amounts of essential amino acids. However, members of the canine family are intolerant to lactose, milk sugar, present in dairy substances, apparently due to an absence of the enzyme lactase in the dog's intestine. Therefore, lactase is provided in an amount of 0.001 to 10 percent by weight and preferably between 1 and 3 percent by weight.

An imitation cheese (sodium casinate), Soymage, and/or vegetable based cheese substance may alternatively be used. Since these cheese substitutes do not contain lactose, the use of the lactose enzyme would not be required in the formulation. The use of these substitute consistuents would further provide the necessary flavoring to make the formulation palatable to pets and would provide economy of manufacture.

Vegetable-based fats are preferably included in an amount from 5 to 10 percent by weight. Examples of such fats include liquid oils or solid hydrogenated vegetable oils such as palm oil, coconut oil, peanut oil or a mixture of various oils. Vegetable oil mixtures generally provide a wide range of fatty acid.

In a further composition of the present invention, animal based fat substances are ommitted entirely. In this composition, the level of vegetable based fat substances are increased to approximately 20 percent by weight. Vegetable based egg substitute and soy based cheese may be utilized to increase paletability. These formulations provide a pure vegetarian or vegan pet diet.

The pet food composition further comprises a hyperfortified vitamin mixture component provided in an amount of 1.75 to 8.0 percent by weight. The vitamin mixture component preferably includes vitamin C, and vitamin E. The complex carbohydrate pectin is also preferably provided in an amount between 0.05 to 5.0 percent by weight.

Vitamin A, D-3, K and B-12 are provided in amounts of at least 5.2 K.I.U., 0.75 K.I.U., 1.0 mg/lb. and 0.25 mg/lb., respectively. The resultant concentrations meet or exceed 400 percent of NRC levels. Additionally, Vitamin E is provided in an amount of approximately 37 I.U./lb., and ascorbic acid in an amount of approximately 0.001 mgs/lb. The following trace minerals are provided in the formulation in approximate mg/lb. quantities:

| Manganese | 26.0 |
|---|---|
| Zinc | 75.0 |
| Iron | 204.0 |
| Copper | 11.0 |
| Cobalt | 0.6 |
| Iodine | 1.4 |
| Magnesium | 864.0 |
| Sulfur | 992.0 |
| Selenium | 0.09 |

The following additional vitamins are provided in approximate mg/lb. quantities:

| Panto Acid | 9.0 |
|---|---|
| Choline | 1081.0 |
| Pyridoxine | 3.0 |
| Folacin | 0.6 |
| Biotin | 0.09 |
| Thiamine | 3.3 |
| Riboflavin | 2.0 |
| Niacin | 9.8 |

Additionally, the composition utilized as cat food must have taurine (sulfonic acid) in an amount of approximately 0.05 percent by weight added. A cat food base mix of vitamins and trace minerals as known in the art is also provided. Synthetic or non-killed animal taurine is preferable.

Further ingredients that may be added to the above formulations include barbecue, imitation fish, tamarine, tomato and/or onion flavoring, as well as imitation cheese and garlic flavorings with approximately triple the amount used in known pet food formulations or in an amount of approximately 0.001 to 15 percent by weight.

The compositions of this invention are preferably mixed and heated in a batch process. Soybean, wheat middling and corn are preferably combined to yield a premix which is blended to form a substantially homogeneous mixture. To the premix is then added vitamins, trace minerals and flavorings. The resultant mixture is then blended a second time. Subsequent to blending, the mixture is extruded into cubes, baked into chunks, formed into pellets, or wet served. Preferably, extrusion is performed by a steam extruder which is heated to approximately 265° F., and which has a forming die for shaping the extruded mixture into cube-shaped units. The extruded cubes are then dried in a dryer. The dried cubes are then shaken to remove fine surface particulates. The cubes are subsequently coated with a layer of fat in a fat applicator.

To more fully illustrate the present invention, the following non-limiting examples are presented.

EXAMPLE 1

Pet food compositions within the scope of the present invention were formed by employing a mixture of the components or ingredients listed in Table 1 shown below, on a percent by weight basis. The compositions of this invention are preferably mixed and heated in a batch process.

Soybean, wheat middling and corn are combined to yield a premix which is blended to form a substantially homogeneous mixture. To the premix is then added vitamins, trace minerals and flavorings. The resultant mixture is then blended a second time.

Subsequent to blending, the mixture is extruded into cubes. Preferably, extrusion is performed by a steam extruder which is heated to approximately 265° F., and which has a forming die for shaping the extruded mixture into cube-shaped units.

The extruded cubes are then dried in a dryer. The dried cubes are then shaken to remove fine surface particulates. The cubes are subsequently coated with a layer of fat in a fat applicator.

TABLE 1

| | |
|---|---|
| Soybean Meal | 27.10 |
| Wheat Middlings | 20.00 |
| Ground Yellow Corn | 17.95 |
| Dried Egg Powder | 10.00 |
| Hydrogenated Vegetable Oil | 10.00 |
| Phosphate dicalcium (18.5%) | 3.15 |
| Yeast | 2.50 |
| Vitamins - Base Mix | 2.50 |
| Dried Whole Whey | 2.50 |
| Pectin | 2.00 |
| Salt | 0.75 |
| Calcium Carbonate | 0.60 |
| Ascorbic Acid | 0.10 |
| Flavoring Mixture | 0.05 |
| Vitamin E (20,000 I.U./lb) | 0.05 |
| Cheese | 0.05 |
| Tomato Flavoring | 0.05 |

The composition produced by the mixture shown in Table 1 was found to have the following approximate nutrient composition on a percent by weight basis.

| | |
|---|---|
| Crude Protein | 30 |
| Digestible Protein | 17 |
| Crude Fat | 8 |
| Crude Fiber | 3 |

EXAMPLE 2

A Pet Food Composition within the scope of the present invention was also formed by employing a mixture of the components listed in Table 2 shown below, on a percent by weight basis. This composition was prepared utilizing the method described with respect to Example 1.

TABLE 2

| | |
|---|---|
| Soybean Meal | 27.05 |
| Wheat Middlings | 20.00 |
| Ground Yellow Corn | 17.95 |
| Cheese | 11.35 |
| Hydrogenated Vegetable Oil | 10.00 |
| Phosphate dicalcium (18.5%) | 3.15 |
| Yeast | 2.50 |
| Vitamins - Base Mix | 2.50 |
| Dried Whole Whey | 2.50 |
| Pectin | 2.00 |
| Salt | 0.75 |
| Ascorbic Acid | 0.10 |
| Flavoring Mixture | 0.05 |
| Vitamin E (20,000 I.U./lb) | 0.05 |
| Tomato Flavoring | 0.05 |

The composition produced by the mixture shown in Table 2 was found to have the following approximate nutrient composition on a percent by weight basis.

| | |
|---|---|
| Crude Protein | 22.0 |
| Crude Fat | 12.0 |
| Crude Fiber | 2.0 |

EXAMPLE 3

A Pet Food Composition within the scope of the present invention was also formed by employing a mixture of the components listed in Table 3 shown below, on a percent by weight basis. This composition was prepared also utilizing the method described with respect to Example 1.

TABLE 3

| | |
|---|---|
| Soybean Meal | 27.05 |
| Ground Yellow Corn | 25.30 |
| Wheat Middlings | 20.00 |
| Cheese | 10.00 |
| Hydrogenated Vegetable Oil | 5.00 |
| Phosphate dicalcium (18.5%) | 3.15 |
| Yeast | 2.50 |
| Vitamins - Base Mix | 2.50 |
| Dried Whole Whey | 2.50 |
| Pectin | 2.00 |
| Lactase | 1.00 |
| Salt | 0.75 |
| Ascorbic Acid | 0.10 |
| Flavoring Mixture | 0.05 |
| Vitamin E (20,000 I.U./lb) | 0.05 |
| Tomato Flavoring | 0.05 |

The composition produced by the mixture shown in Table 3 was found to have the following approximate nutrient composition on a percent by weight basis.

| | |
|---|---|
| Crude Protein | 30.00 |
| Crude Fat | 10.00 |
| Crude Fiber | 2.00 |

EXAMPLE 4

A Pet Food Composition within the scope of the present invention was also formed by employing a mixture of the components listed in Table 4 shown below, on a percent by weight basis. This composition was prepared also utilizing the method described with respect to Example 1.

TABLE 4

| | |
|---|---|
| Soybean Meal | 27.10 |
| Hydrogenated Vegetable Oil | 20.65 |
| Wheat Middlings | 20.00 |
| Ground Yellow Corn | 17.95 |
| Phosphate dicalcium (18.5%) | 3.15 |
| Yeast | 2.50 |
| Vitamins - Base Mix | 2.50 |
| Imitation Cheese | 2.50 |
| Pectin | 2.00 |
| Salt | 0.75 |
| Calcium Carbonate | 0.60 |
| Ascorbic Acid | 0.10 |
| Flavoring Mixture | 0.05 |
| Vitamin E (20,000 I.U./lb) | 0.05 |
| Tomato Flavoring | 0.05 |

The composition produced by the mixture shown in Table 4 was found to have the following approximate nutrient composition on a percent by weight basis.

| | |
|---|---|
| Crude Protein | 30 |
| Digestible Protein | 17 |
| Crude Fat | 8 |
| Crude Fiber | 3 |

As many changes are possible to the embodiments of this invention utilizing the teachings thereof, the descriptions above should be interpreted in the illustrative and not the limited sense.

That which is claimed is:

1. A pet food composition substantially free of meat consisting essentially of:
   a. a mixture of proteinaceous and farinaceous components in an amount sufficient to provide a nutritionally balanced diet;
   b. a non-meat based animal fat substance, said non-meat based animal fat substance being a dairy based fat substance provided in an amount between 8-22 percent by weight,
   c. vegetable oil in an amount between 5 and 10 percent by weight;
   d. Vitamins and minerals in amounts sufficient for intestinal absorption of nutrients; and
   e. an amount of lactase of between 0.001 and 10 percent by weight.

2. The pet food composition of claim 1, wherein sufficient to metabolize lactose, wherein said pet food composition provides a palatable nutritive ration in dry pellet form said proteinaceous and farinaceous mixture is provided in an amount of between 10 and 30 percent by weight.

3. The pet food composition of claim 1, wherein said dairy based fat substance is selected from the group consisting of butter, cheese, milk fat, or whey.

4. The pet food composition of claim 1, further consisting essentially of a hyperfortified vitamin mixture.

5. The pet food composition of claim 4, wherein said vitamin mixture is provided in an amount of 1.75 to 8.0 percent by weight.

6. The pet food composition of claim 4, wherein said vitamin mixture includes vitamin C and vitamin E.

7. The pet food composition of claim 1, further consisting essentially of pectin in an amount of between 0.01 and 5.0 percent by weight.

8. The pet food composition of claim 1, further consisting essentially of taurine in an amount of approximately 0.05 percent by weight.

9. The pet food composition of claim 1, wherein said proteinaceous components are selected from the group consisting of soybean meal, wheat middlings, corn gluten meal and rice gluten meal.

10. The pet food composition of claim 1, wherein said farinaceous components are selected from the group consisting of ground corn, oats, rice, barley, and wheat flour.

11. The pet food composition of claim 1, further consisting essentially of a flavoring substance selected from the group consisting of barbecue, imitation fish, onion, tamarine, tomato, cheese and garlic.

12. The pet food composition of claim 11, wherein said flavoring substance is provided in an amount of 0.001 to 15 percent by weight.

* * * * *